United States Patent [19]

Sebag et al.

[11] Patent Number: 4,960,772
[45] Date of Patent: Oct. 2, 1990

[54] BENZOYL PEROXIDE AND QUATERNARY AMMONIUM BASED PHARMACEUTICAL AND COSMETIC COMPOSITIONS

[75] Inventors: Henri Sebag, Paris; Irina Beck, Villepinte, both of France

[73] Assignee: L'Oreal, Paris, France

[21] Appl. No.: 314,659

[22] Filed: Feb. 23, 1989

[30] Foreign Application Priority Data

Mar. 9, 1988 [FR] France ............... 88 03042

[51] Int. Cl.$^5$ ............................. A61K 31/14
[52] U.S. Cl. .................. 514/231.2; 514/358; 514/396; 514/554; 514/555; 514/714
[58] Field of Search ............... 514/714, 358, 554, 555, 514/396, 231.2; 252/98

[56] References Cited

U.S. PATENT DOCUMENTS

| | | | |
|---|---|---|---|
| 2,852,434 | 9/1958 | Taylor | 514/231.2 |
| 2,865,805 | 12/1958 | Frant | 514/555 |
| 3,852,210 | 12/1974 | Krezanoski | 252/102 |
| 3,886,278 | 5/1975 | Gallo | 514/358 |
| 3,890,227 | 7/1975 | McFarland | 514/358 |
| 4,021,572 | 5/1977 | Van Scott | 514/554 |
| 4,167,487 | 9/1979 | Gray | 514/714 |
| 4,330,551 | 5/1982 | Stout et al. | 514/396 |
| 4,361,584 | 11/1982 | Fulton | 514/714 |
| 4,387,107 | 6/1983 | Klein | 514/714 |
| 4,446,145 | 5/1984 | Van Bever | 514/396 |
| 4,547,305 | 10/1985 | Cornelissen et al. | 252/95 |
| 4,692,329 | 9/1987 | Klein | 514/714 |
| 4,737,307 | 4/1988 | Brown et al. | 514/358 |
| 4,803,228 | 2/1989 | Jacquet et al. | 514/714 |
| 4,804,531 | 2/1989 | Grollier . | |
| 4,906,617 | 3/1990 | Jacquet et al. | 514/714 |

FOREIGN PATENT DOCUMENTS 1163044  9/1969 United Kingdom .

*Primary Examiner*—Donald Daus
*Attorney, Agent, or Firm*—Marshall, O'Toole, Gerstein, Murray & Bicknell

[57] ABSTRACT

A pharmaceutical and cosmetic composition for topical application comprises in a physiologically acceptable medium a combination of benzoyl peroxide and a quaternary ammonium salt selected from a quaternary ammonium alkyl sulfate of sulfonate, an aryl sulfonate and an alkyl aryl sulfonate.

18 Claims, No Drawings

BENZOYL PEROXIDE AND QUATERNARY AMMONIUM BASED PHARMACEUTICAL AND COSMETIC COMPOSITIONS

BACKGROUND OF THE INVENTION

1. Field of the Invention

The present invention concerns benzoyl peroxide and quaternary ammonium based pharmaceutical and cosmetic compositions and their use, particularly in the treatment of acne.

2. Description of the Prior Aart

The etiopathology of acne is not well understood but acne is known to start with formation of a characteristic lesion: the comedo. This arises from obstruction of the pilosebaceous canal following dyskeratinization of the infundibular zone of the canal. A major effect of the obstruction is hyperproliferation of the resident cutaneous strains which precipitates an inflammation reaction in the organism.

Benzoyl peroxide is a known therapeutic agent for treatment of acne and has been known for several years to be a particularly interesting keratolytic agent. Amongst other qualities, it has good bacteriostatic properties.

Conventional antibiotics are also very widely used in treating acne. They possess significant bacteriostatic and anti-inflammatory properties. Oral active antibiotics are plentiful and some, for example clindamycin and especially erythromycin, may be used topically.

Benzoyl peroxide has been combined with antibiotics to improve the efficacy of anti-acne compositons. In particular, benzoyl peroxide has been combined with erythromycin (FR-A-2 378 523).

Whether or not combined with benzoyl peroxide, however, antibiotics suffer from a major drawback with prolonged use in that they render the bacterial flora resistant. They thus become relatively inactive during subsequent treatment (J. J. LEYDEN, J. Am. Acad. Dermatol. 8, (1), 41–45 (1983)).

In addition, combinations of benzoyl peroxide and erythromycin have proved to be unstable when stored.

Replacement of the antibiotics by quaternary ammonium salts has been suggested for topical treatment of acne (M. GLOOR, Arch. Dermatol. Res. 265, 207–212 (1979)). Some quaternary ammonium salts are just as effective as antibiotics against the principal strains causing acne without inducing resistance.

Stable detergent compositions for cleansing the skin have also been described. These may contain both a surfactant quaternary ammonium compound such as benzalkonium, cetalkonium, cetylpyridinium or benzethonium chloride, or cethexonium bromide, plus benzoyl peroxide (U.S. Pat. No. 3,852,210).

The combination of benzoyl peroxide with any of the quaternary ammonium salts cited in the above patent has been found to degrade after a few hours at room temperature, however.

It has now been discovered, surprisingly, that stable compositions for the treatment of acne, cutaneous ulcers and the general treatment of dermatioses and cutaneous disorders can be obtained by combining benzoyl peroxide with certain quaternary ammonium derivatives.

Benzoyl peroxide can be used in small amounts in such inventive combinations because of the latter's high stability, with an advantageous improvement in cutaneous tolerance.

Compositions according to the invention are tolerated well by the system. They possess very good antibacterial properties without inducing strain resistance, they are keratolytic, bacteriostatic (particularly with respect to one of the main acne-causing germs, propionibacterium Acnes) and effective in the treatment of and reducing the number of comedos.

Because of their properties, compositions according to the invention may be used to treat cutaneous disorders and dermatoses, particularly acne and cutaneous ulcers.

An object of the present invention is, therefore, the provision of a topical pharmaceutical and/or cosmetic composition containing benzoyl peroxide and at least one quaternary ammonium salt such as, for example, those described below.

Another object of the invention is a cosmetic treatment method using such a composition.

SUMMARY OF THE INVENTION

In one aspect the invention consists in a composition for topical application that contains in a physiologically acceptable medium benzoyl peroxide and a quaternary ammonium salt selected from the group consisting of a quaternary ammonium alkyl sulfate or sulfonate, an aryl sulfonate and an alkyl aryl sulfonate.

In particular, the quaternary ammonium alkyl sulfates or sulfonates, aryl sulfonates or alkyl aryl sulfates combined according to the invention with benzoyl peroxide are primarily those having the following general formula (I):

wherein:

(a) $R_1$ represents the group:

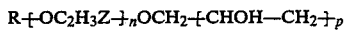

where $0 \leq n \leq 6$ and $p$ is 0 or 1;

R represents a $C_8$ to $C_{32}$ alkyl, alkylcycloalkyl or alkylaryl radical wherein the aliphatic chain may be interrupted by an ether, amide, sulfonamide or carbamate group and/or contain a hydroxyl substituent; when n is other than 0, Z represents H, $CH_3$ or $CH_2OH$, when Z represents H or $CH_3$, $p=0$; when Z represents $CH_2OH$, $p=1$. The group $(OC_2H_3Z)$ may represent one and/or the other of the following structures:

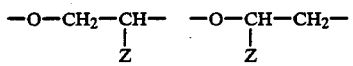

(b) $R_2$ represents a $C_1$ to $C_{22}$ alkyl radical which may comprise one or more hydroxyl groups.

(c) $R_3$ represents a $C_1$ to $C_6$ alkyl radical, a $C_1$ to $C_6$ monohydroxyalkyl radical, a $C_3$ to $C_6$ polyhydroxyalkyl radical or a benzyl radical.

(d) $R_4$ represents a $C_1$ to $C_{18}$ alkyl or alkyloxy radical.

(e) $R_2$ and $R_3$ may together form a heterocycle such as piperidine or morpholine with a nitrogen atom.

(f) $R_1$, $R_2$ and $R_3$ may form a pyridine, methylpyridine or hydroxypyridine cycle with a nitrogen atom.

In each case, $X^-$ represents an alkyl sulfate or sulfonate, aryl sulfonate or alkyl aryl sulfonate anion.

Particularly preferred anions are those selected from the following group:

$CH_3OSO_3^\ominus$, $C_2H_5OSO_3^\ominus$, $CH_3SO_3^\ominus$,

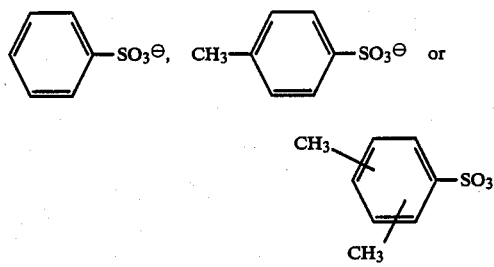

Particularly preferred quaternary ammonium compounds are the alkyl sulfates or sulfonates, aryl sulfonates or alkyl aryl sulfonates of:
trimethyl lauryl ammonium,
dimethyl hydroxyethyl cetyl ammonium,
dimethyl methoxy lauryl ammonium,
trimethyl laurylamido propyl ammonium,
cetylpyridinium,
cetyloxypyridinium,
dimethyl benzyl cetyl ammonium,
dimethyl benzyl octylphenoxyethoxyethyl ammonium,
dimethyl hydroxycyclohexyl cetyl ammonium,
N-methyl,N'-cetyl imidazolium,
methyllaurylmorpholinium.

The composition may be in the form of a solution, emulsion, suspension, gel or dispersion containing at least one compound having formula (I) in a concentration of between 0.01 and 25% by weight and preferably between 0.1 and 5% by weight with respect to the total composition weight. Benzoyl peroxide may be present in a concentration of between 0.1 and 20% by weight, preferably between 0.5 and 10% by weight with respect to total composition weight.

These compositions may contain known physiologically acceptable media and additives. Solutions, emulsions, microsuspensions or vesicular dispersions may, for example, be prepared using one or more physiologically acceptable organic supports selected from water, ethanol, isopropanol, polyglycol or glycol ethers, polyalkylene glycols, natural or synthetic oils such as triglycerides, fatty alcohols or fatty acid esters.

Compositions according to the invention may also contain foam or emulsion surfactants, polymers such as cellulose and its derivatives, guar gum, heterobiopolysaccharides, polyacrylic acids and their derivatives, poly-$\beta$-alanine, ethers or esters of polyethyleneglycols, colloidal silica, superfatting agents, emollients, wetting agents, pH regulators, penetrating agents, preservatives, UV screens perfumes, dyes and/or pigments intended to color the skin or the composition itself, and any other ingredient normally used in compositions intended for topical application.

Excipients and ingredients which could react unfavorably with benzoyl peroxide used in accordance with the invention must not be used, of course.

Compositions according to the invention may also contain anti-acne agents such as retinoic derivatives, antibacterial agents, anti-inflammation agents, non-hormonal steroids particularly pregnenolone and/or keratolytic or comedolytic agents.

Galenic forms such as solutions, creams, milks, gels, dispersions or microemulsions (thickened or otherwise), impregnated pads, ointments, sticks or soap tablets are particularly suitable for topical application.

Pharmaceutical compositions in accordance with the invention may be used as a medicament in therapeutic treatment of dermatoses, particularly acne, primarily because of their antibacterial and keratolytic properties.

In another aspect the invention therefore consists in the use of pharmaceutical compositions as specified hereinabove in the preparation of a medicament for the treatment of dermatoses, in particular acne, cutaneous ulcers, warts and skin dyskeratinizations.

Compositions in accordance with the invention may be used for cosmetic skin treatment, particularly as a cleansing and disinfecting, comedolytic or keratolytic product.

In a further aspect the invention consists in a cosmetic treatment method which includes applying to the skin in order to cleanse or purify it a composition as specified hereinabove.

Acne treatment may be effected by applying the composition to the affected areas once or twice a day over a period of twelve weeks.

DESCRIPTION OF THE INVENTION

The following examples are intended to illustrate the invention without limiting its scope in any way.

EXAMPLES

Example 1

The following composition was prepared:

| | |
|---|---|
| PEG 50 stearate | 4.00 g |
| Glycerol monostearate | 1.00 g |
| Stearyl alcohol | 1.00 g |
| Cetyl alcohol | 1.00 g |
| Perhydrosqualene | 12.00 g |
| Hydroxyethylcellulose | 0.30 g |
| Methyl parahydroxybenzoate | 0.10 g |
| Buffer qsp pH 6 | |
| EDTA disodium salt | 0.05 g |
| Benzoyl peroxide | 5.00 g |
| Dodecyl pyridinium p-toluenesulfonate | 0.70 g |
| Water qsp | 100.00 g |

This composition was applied in the form of a dermal cream, once or twice a day over a period of one to twelve weeks.

EXAMPLE 2

| | |
|---|---|
| Hydroxyethylcellulose | 0.80 g |
| Polysorbate 20 (Sorbitan monolaurate of polyoxyethylene (20)) | 2.50 g |
| Benzoyl peroxide | 5.00 g |
| Dimethyl/methoxy/lauryl ammonium methyl sulfate | 0.50 g |
| Glycerine | 3.00 g |
| Buffer qsp pH 6 | |

-continued

| | |
|---|---|
| Water qsp | 100.00 g |

This composition was applied in the form of a lotion, once or twice a day until the lesions caused by acne had disappeared.

EXAMPLE 3

| | |
|---|---|
| Hydroxyethylcellulose | 1.00 g |
| Propyleneglycol | 3.00 g |
| Benzoyl peroxide | 10.00 g |
| Trimethyl lauryl ammonium methyl sulfate | 1.00 g |
| Ethanol, 95° | 10.00 g |
| Poloxamer 182 (copolymer of polyoxyethylene/polyoxypropylene having formula: HO(CH$_2$CH$_2$O)$_x$(CHCH$_2$O)$_y$—(CH$_2$CH$_2$O)$_z$—H 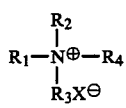 where x = 8, y = 30, z = 8) | 0.30 g |
| EDTA disodium salt | 0.05 g |
| Buffer qsp pH 6 | |
| Water qsp | 100.00 g |

This composition was applied in the form of a dermal gel twice a day to affected areas of the skin.

We claim:

1. A composition for topical application consisting essentially of benzoyl peroxide and a quaternary ammonium salt selected from the group consisting of a quaternary ammonium alkyl sulfate, alkyl sulfonate, benzene sulfonate and alkylbenzene sulfonate as active ingredients in a physiologically acceptable medium.

2. A composition according to claim 1 wherein said quaternary ammonium salt has the formula (I):

$$\begin{array}{c} R_2 \\ | \\ R_1-N^\oplus-R_4 \\ | \\ R_3X^\ominus \end{array} \quad (I)$$

wherein (a) $R_1$ represents the group:

where $0 \leq n \leq 6$ and p is 0 or 1;

R represents a $C_8$ to $C_{32}$ alkyl, alkylcycloalkyl or alkylaryl radical wherein the aliphatic chain may be interrupted by an ether, amide, sulfonamide or carbamate group or contains a hydroxyl substituent; when n is other than 0, Z represents H, CH$_3$ or CH$_2$OH; when Z represents H or CH$_3$, p=0, when Z represents CH$_2$OH, p=1; and group (OC$_2$H$_3$Z) may represent either of the following structures:

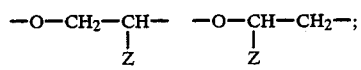

(b) $R_2$ represents a $C_1$ to $C_{22}$ alkyl radical which may be substituted by one or more hydroxyl groups;

(c) $R_3$ represents a $C_1$ to $C_6$ alkyl radical, a $C_1$ to $C_6$ monohydroxylalkyl radical, a $C_3$ to $C_6$ polyhydroxylalkyl radical or a benzyl radical;

(d) $R_4$ represents a $C_1$ to $C_{18}$ alkyl or alkyloxy radical;

(e) $R_2$ and $R_3$ may together form a piperidine or morpholine ring with the nitrogen atom;

(f) $R_1$, $R_2$ and $R_3$ may together form an imidazole, a pyridine, a methylpyridine or a hydroxypyridine ring with the nitrogen atom; and $X^\ominus$ represents an alkylsulfate, alkyl sulfonate, benzene sulfonate, or alkylbenzene sulfonate anion.

3. A composition according to claim 2 wherein said anion $X^-$ is selected from the group comprising the following formulas:

$CH_3OSO_3^\ominus$, $C_2H_5OSO_3^\ominus$, $CH_3SO_3^\ominus$,

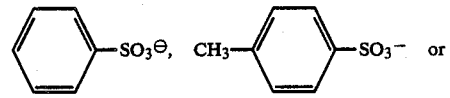 or

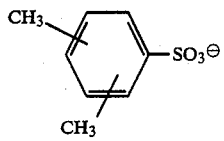

4. A composition according to claim 3 wherein said quaternary ammonium salt corresponding to formula (I) is selected from the group comprising the trimethyl lauryl ammonium, dimethyl hydroxyethyl cetyl ammonium, dimethyl methoxy lauryl ammonium, trimethyl laurylamido propyl ammonium, cetylpyridinium, cetyloxypyridinium, dimethyl benzyl cetyl ammonium, dimethyl benzyl octylphenoxyethoxyethyl ammonium, dimethyl hydroxycyclohexyl cetyl ammonium, N-methyl,N'-cetyl imidazolium or methyllaurylmorpholinium.

5. A composition according to claim 4 wherein said benzoyl peroxide is present in proportions of 0.1 to 20% by weight with respect to total composition weight.

6. A composition according to claim 5 wherein said quaternary ammonium salt corresponding to formula (I) is present in proportions of 0.01 to 25% by weight with respect to total composition weight.

7. A composition according to claim 5 wherein said benzoyl peroxide is present in proportions of 0.5 to 10% by weight with respect to total composition weight.

8. A composition according to claim 6 wherein said quaternary ammonium salt corresponding to formula (I) is present in proportions of 0.1 to 5% by weight with respect to total composition weight.

9. A composition according to claim 1 for use as a medicament wherein said physiologically acceptable medium is a pharmaceutically acceptable medium.

10. A composition according to claim 1 wherein said physiologically acceptable medium is a cosmetically acceptable medium.

11. A composition according to claim 1 in the form of a gel, solution, dispersion, emulsion or suspension.

12. A composition according to claim 1 in the form of a cream, milk, gel, impregnated pad, ointment, stick or soap tablet.

13. A composition according to claim 1 further containing at least one retinsic derivative.

14. A composition according to claim 1 further containing at least one UV screen.

15. Method of treating dermatoses comprising applying topically to the skin a composition consisting essentially of effective quantities of benzoyl peroxide and a quaternary ammonium salt selected from the group consisting of a quaternary ammonium alkyl sulfate, alkyl sulfonate, benzene sulfonate and alkylbenzene sulfonate as active ingredients in a physiologically acceptable medium.

16. Method of treating cutaneous ulcers, warts and skin dyskeratinizations comprising topically applying thereto a composition consisting essentially of effective quantities of benzoyl peroxide and a quaternary ammonium salt selected from the group consisting of a quaternary ammonium alkyl sulfate, alkyl sulfonate, benzene sulfonate and alkylbenzene sulfonate as active ingredients in a physiologically acceptable medium.

17. Method of treating acne comprising topically applying thereto a composition comprising in a physiologically consisting essentially of effective quantities of benzoyl peroxide and a quaternary ammonium salt selected from the group consisting of a quaternary ammonium alkyl sulfate, alkyl sulfonate, benzene sulfonate and alkylbenzene sulfonate as active ingredients in a physiologically acceptable medium.

18. A method of cosmetic treatment to cleanse and purify the skin consisting in applying thereto a composition comprising, in a cosmetically acceptable medium, benzoyl peroxide and a quaternary ammonium salt selected from the group comprising a quaternary ammonium alkyl sulfate or sulfonate, an aryl sulfonate and an alkyl aryl sulfonate.

* * * * *